(12) United States Patent
Asai et al.

(10) Patent No.: US 8,834,937 B2
(45) Date of Patent: Sep. 16, 2014

(54) BONE FILLING MATERIAL COMPRISING SINTERED TITANIUM DIOXIDE AND DEXTRIN AND METHOD FOR RECONSTRUCTING BONE DEFECTS USING THE SAME

(75) Inventors: Takafumi Asai, Nagoya (JP); Tatsushi Kawai, Nagoya (JP)

(73) Assignees: Aichi Gakuin, Aichi (JP); Matsutani Chemical industry Co., Ltd., Hyogo (JP)

( * ) Notice: Subject to any disclaimer, the term of this patent is extended or adjusted under 35 U.S.C. 154(b) by 275 days.

(21) Appl. No.: 12/879,858

(22) Filed: Sep. 10, 2010

(65) Prior Publication Data

US 2012/0064172 A1     Mar. 15, 2012

(51) Int. Cl.
*A61K 33/24*     (2006.01)
*A61P 19/00*     (2006.01)
*A61K 8/29*     (2006.01)
*A61L 27/42*     (2006.01)

(52) U.S. Cl.
CPC ........... *A61L 27/427* (2013.01); *A61L 2430/02* (2013.01)
USPC ........... 424/617; 424/488; 424/493; 424/635; 514/58; 514/492

(58) Field of Classification Search
CPC ...... A61L 2430/02; A61L 27/427; A08L 3/02
USPC ............. 424/617, 488, 493, 635; 514/58, 492
See application file for complete search history.

(56) References Cited

U.S. PATENT DOCUMENTS

| | | | |
|---|---|---|---|
| 3,504,437 A * | 4/1970 | Siegel | 433/202.1 |
| 2010/0104689 A1* | 4/2010 | Thorengaard | 426/5 |
| 2011/0129544 A1 | 6/2011 | Miyazaki et al. | |
| 2012/0046385 A1* | 2/2012 | Nakamura et al. | 523/116 |

FOREIGN PATENT DOCUMENTS

| | | | |
|---|---|---|---|
| JP | 2009-077789 A | | 4/2009 |
| JP | 2009-178391 A | | 8/2009 |
| WO | WO 2006025777 | * | 3/2006 |
| WO | 2008/102568 A1 | | 8/2008 |
| WO | WO 2010077128 | * | 7/2010 |
| WO | WO 2010098304 | * | 9/2010 |

* cited by examiner

*Primary Examiner* — Mina Haghighatian
(74) *Attorney, Agent, or Firm* — Sughrue Mion, PLLC

(57) ABSTRACT

A bone filling material comprising sintered titanium dioxide and dextrin and a method for reconstructing bone defects which comprises filling the bone defects in an animal with the bone filling material. The bone filling material of the invention has excellent cell compatibility, biocompatibility and shape-imparting property.

8 Claims, 9 Drawing Sheets

BONE FILLING MATERIAL COMPRISING SINTERED TITANIUM DIOXIDE AND DEXTRIN AND METHOD FOR RECONSTRUCTING BONE DEFECTS USING THE SAME

FIELD OF THE INVENTION

This invention relates to a bone filling material comprising sintered titanium dioxide and dextrin and method for reconstructing bone defects in an animal using the same.

BACKGROUND ART

For reconstructing bone defects in dental and orthopedic fields, autogenous bone grafts have been clinically applied as most assured method. However, it is necessary to operatively invade healthy region to collect bone grafts, and the amount of collected bone grafts is limited. In addition, function disorder may be caused in bone collected region, and post graft infection and/or bone resorption may be occurred. Therefore, there is a need for artificial bone filling materials in place of autogenous bone.

For reconstructing bone defects in dental and orthopedic fields, methods using artificial bone filling materials in place of autogenous bone have been clinically applied. However, if powdery or particulate bone filling materials are filled, there is a concern that the materials will easily leak out from the filled regions. In addition, because bone filling materials do not have shape-imparting properties when used alone, it is difficult to keep the materials retained in the bone defect regions for a certain period of time while maintaining an appropriate morphology.

To improve these disadvantages, there are trials to develop new composite materials comprising bone filling material and a polymer material. There have been reported that various polymers are used as shape-imparting agent to make a composite with bone filling material and the composite is filled into bone defects. Most of these composites use natural protein as a natural polymer material and therefore they are required to have safety including antigenicity and have not often been applied clinically.

Moreover, as artificial bone filling materials for reconstructing bone defects, calcium phosphate materials such as hydroxyapatite and tri-calcium phosphate have been clinically applied. These materials promote bone formation to replace bone tissue but often cause bone resorption after operation. Generally, bone filling materials work as scaffold for bone reconstruction but do not show active promotion of bone formation.

JP-A-2009-077789 discloses a method for easily preparing bone filling materials which comprises drying a slurry containing calcium phosphate powder to form a green body which is then pulverized and sintered.

JP-A-2009-178391 discloses bone filling materials having improved handling property during filling operation and high biocompatibility, which comprise a mixture of liquid L-oligolactic acid, liquid D-oligolactic acid and calcium phosphate powder or granule.

WO2008/102568 discloses a mixture of; a bone/cartilage formation-stimulating agent comprising sulfated galactosaminoglycan having 0.6 or more sulfate ester groups on average per one constituent monosaccharide or a salt thereof as an active ingredient; and a factor having a bone/cartilage formation-stimulating activity or a bone filling material (BMP, TGF-$\beta$, FGF, IGF, insulin, PDGF, HGF, midkine, pleiotrophin, collagen, gelatin, proteoglycan, fibronectin, osteocalcin, osteopontin, osteonectin, bone sialoprotein, hydroxyapatite, dicalcium phosphate anhydride, dicalcium phosphate dihydrate, $\alpha$-tricalcium phosphate, amorphous calcium phosphate, octacalcium phosphate, $\beta$-tricalcium phosphate, PLLA, PLGA, titanium, decalcified bone, autogenous bone, etc.).

SUMMARY OF THE INVENTION

Under such circumstances, the present invention has been completed. An object of the invention is to provide a bone filling material having excellent cell compatibility, biocompatibility, and shape-imparting property and well work as a scaffold for bone formation; and a method for reconstructing bone defects in an animal using the same.

Means for Solving the Problems

Taking the above points into account, the inventers of this invention have conducted various experiments and found that a mixture of sintered titanium dioxide and dextrin has excellent properties as a bone filling material and based on this finding, they have completed the present invention.

The present invention provides a bone filling material and a method for reconstructing bone defects as shown below.

1. A bone filling material comprising sintered titanium dioxide and dextrin.
2. The bone filling material of item 1, which comprises 0.5 to 10 parts by weight of the dextrin and 70 to 170 parts by weight of water per 100 parts by weight of the sintered titanium dioxide.
3. The bone filling material of item 1, wherein the sintered titanium dioxide is of rutile-type.
4. The bone filling material of item 1, wherein the dextrin is indigestible dextrin or its reductant.
5. A method for reconstructing bone defects which comprises filling the bone defects in an animal with bone filling material comprising sintered titanium dioxide and dextrin.
6. The method of item 5, wherein the bone filling material comprises 0.5 to 10 parts by weight of the dextrin and 70 to 170 parts by weight of water per 100 parts by weight of the sintered titanium dioxide.
7. The method of item 5, wherein the sintered titanium dioxide is of rutile-type.
8. The method of item 5, wherein the dextrin is indigestible dextrin or its reductant.

The bone filling material of the present invention comprises sintered titanium dioxide and dextrin. Sintered titanium dioxide is chemically stable material which is not attacked by acid or alkali at room temperature and it has similar levels of bone conduction capability as existing bone filling materials. In addition, as explained later, dextrin has excellent cell compatibility and can be diluted with physiological saline and etc. to use as shape-imparting material. Thus, the bone filling material of the invention has high biocompatibility and well works as a scaffold for bone formation. In addition, the bone filling material of the invention stimulates bone formation and rarely causes bone resorption after operation.

BRIEF DESCRIPTIONS OF THE DRAWINGS

FIGS. 4A to 4D show the results of histological observation of bone tissues filled with sintered titanium dioxide-dextrin complex or BONE JECT®. In each figure, the right figure is a macrograph of the framed area of the left figure and black areas show the bone filling material which surrounded by bone tissue. Histological observation of bone tissues one week after implantation revealed that the bone tissue was firmly filled with sintered titanium dioxide-dextrin complex (FIG. 4A) or BONE JECT® (FIG. 4B) but was almost not reconstructed. Meanwhile, six weeks after implantation, it was observed that bone tissues were clearly reconstructed between particles for both the samples (FIG. 4C (sintered titanium dioxide-dextrin complex) and FIG. 4D (BONE JECT®)).

Figure 5A:
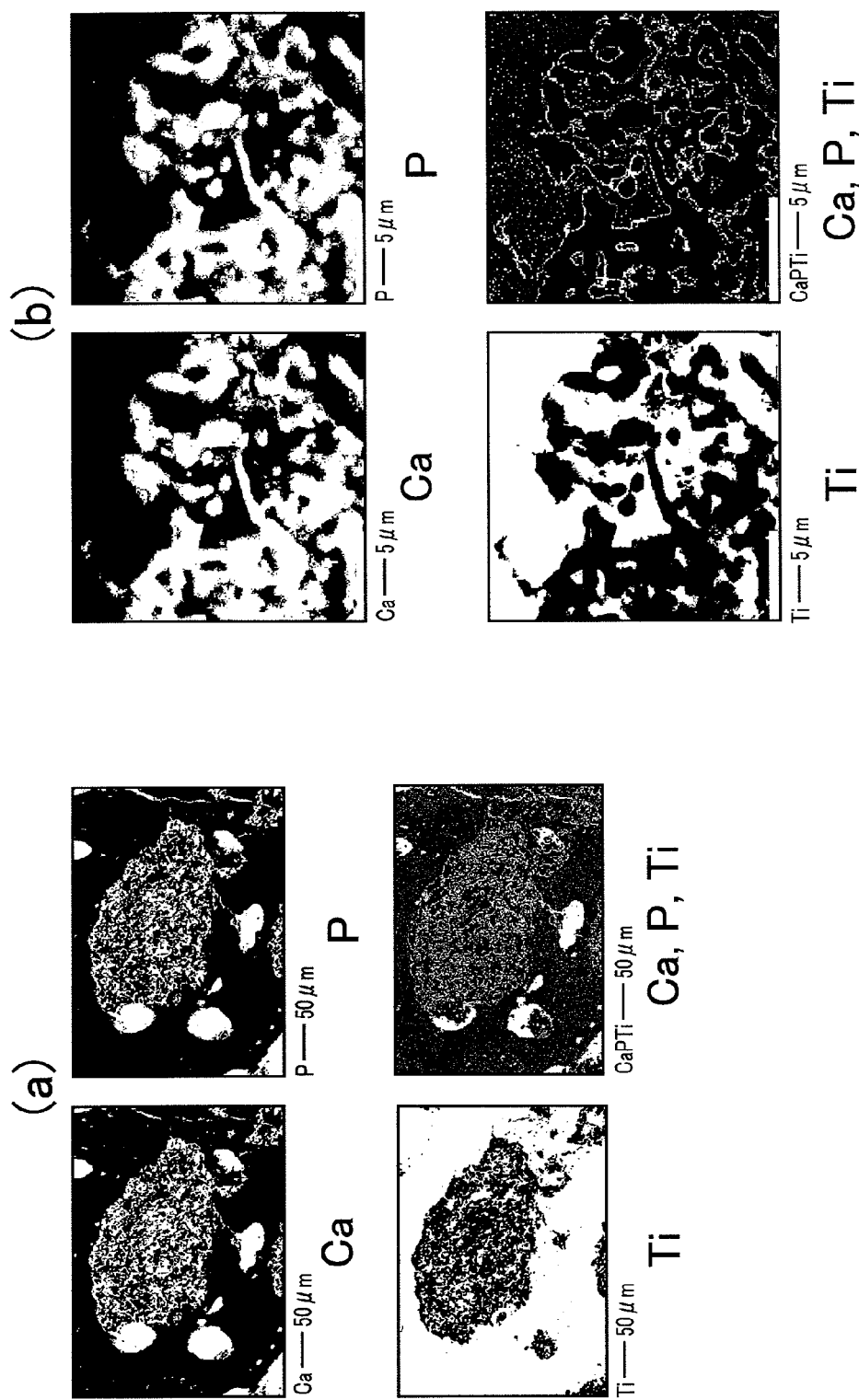
Figure 5B:
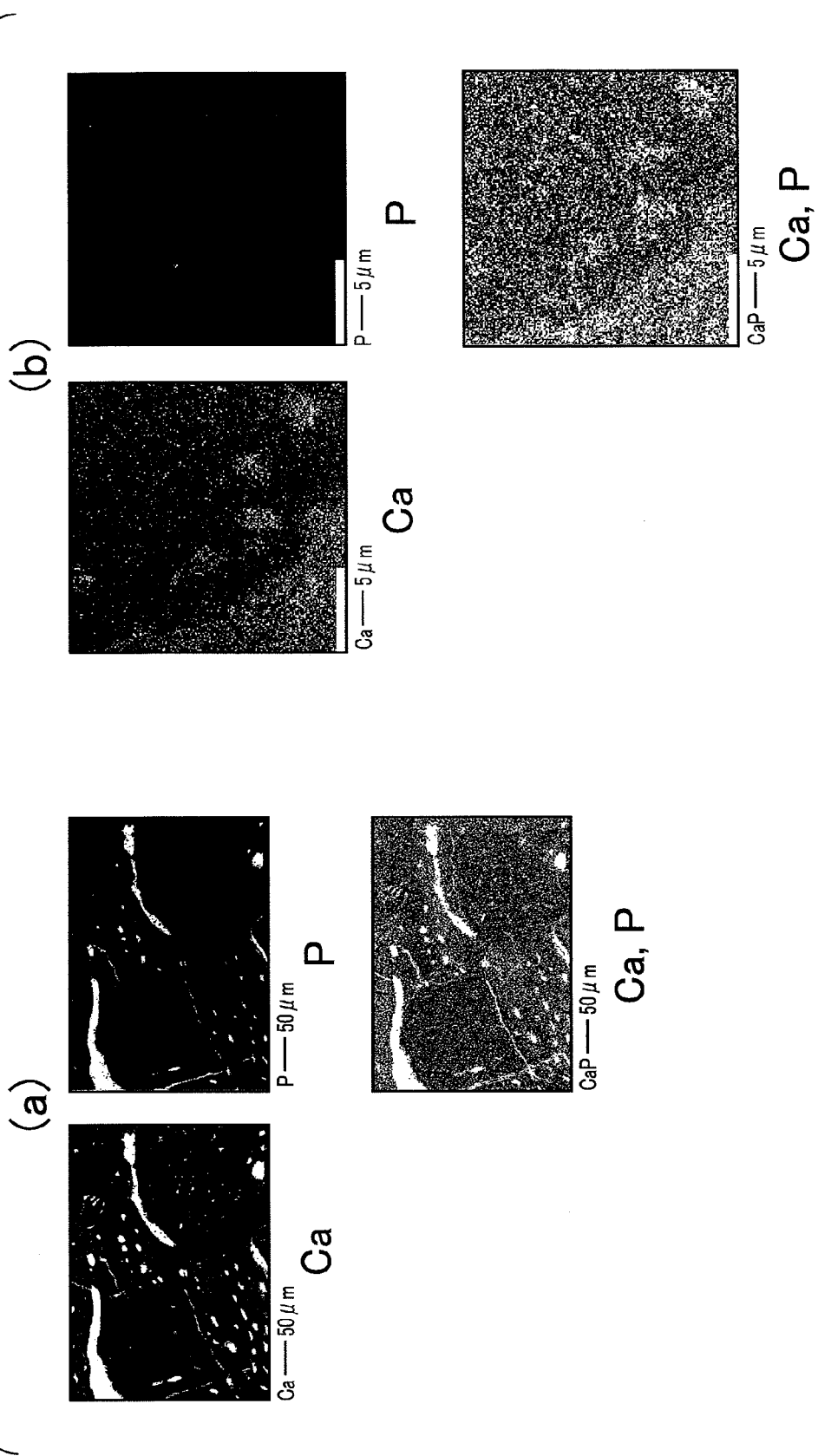

FIGS. 5A and 5B show the results observed under Electron Probe Micro Analyzer (EPMA) for the samples six weeks after implantation. In FIGS. 5A and 5B, (b) (3000 fold) is a partial micrograph of (a) (300 fold). In FIG. 5A (sintered titanium dioxide-dextrin complex) and FIG. 5B (BONE JECT®), black areas show the presence of Ca, P, Ti and Ca+P+Ti. It was confirmed that Ca and P were present in porous inner areas between the sintered titanium dioxide particles.

DETAILED DESCRIPTIONS OF THE INVENTION

Examples of sintered titanium dioxide ($TiO_2$) which can be used in the invention include rutile-type and anatase-type of tetragonal system and brookite-type of orthorhombic system. However, rutile-type is preferred because it is stable at all temperature range from room temperature to melting point. Titanium dioxide has excellent durability and is chemically stable material which is not attacked by acid or alkali at room temperature. It is non-absorptive material and expected to be applied in medical field. It has been used as a raw material for white paints, pigments, medicaments and cosmetics. It is also a starting material for smelting of metallic titanium. It is known that titanium dioxide is formed as oxide coating for artificial fang (implant) in dental field.

It has been demonstrated that rutile-type titanium dioxide, in particular, titanium dioxide sintered at 1300 to 1500° C. for 30 minutes, for example, at about 1400° C. for 30 minutes has excellent cell compatibility. In contrast, titanium dioxide which is not sintered is particles of nano level and therefore there is a fear that cells may phagocytize the particles.

For the reasons above, titanium dioxide used in the present invention is preferably sintered one. It is considered that biocompatibility and bone conduction capability of titanium dioxide will be increased by sintering at about 1400° C. The term "bone conduction capability" means a property which stimulates proliferation of odontogenic cells and synthesis of collagen fiber to promote bone formation. In this connection, promotion of bone formation is limited to within bone tissues.

A diameter of sintered titanium dioxide used in the invention is not limited but preferably is in the range of 10 to 60 μm, more preferably 30 to 50 μm.

Dextrin used in the present invention is a kind of a polymer of D-glucose and a polysaccharide having intermediate complexity between starch and maltose. A degree of polymerization (average degree of polymerization) of dextrin used in the present invention is preferably 3 to 30, more preferably 3 to 15. If it is smaller than 3, it may be difficult to make a bulk, while if it is larger than 30, it may become too viscous and it may be difficult to handle.

Dextrin used in the present invention may be those having α-1,4-glycosidic bonds only, or those having α-1,4- and α-1,6-glycosidic bonds only, or those having α-1,2-glycosidic bonds or α-1,3-glycosidic bonds in addition to the above glycosidic bonds.

Dextrin used in the present invention may be those which are water soluble and are digested in a human body and whose viscosity can be easily adjusted. Dextrin used in the present invention may also be branched dextrin or indigestible dextrin which have branched structures which are hardly digested in a human body. Indigestible dextrin has α-1,6-glycosidic bonds, α-1,2-glycosidic bonds and α-1,3-glycosidic bonds in addition to α-1,4-glycosidic bonds in its structure (so-called "branched structure"), and it is resistant to human body enzymes.

In addition, dextrin used in the present invention may also include reduced dextrin or reduced indigestible dextrin which are obtained by hydrogenating (so-called "reducing") a reducing terminal of sugar molecule of dextrin or indigestible dextrin. Commercially available products include Pinefiber, Fibersol-2, Fibersol-2H, Pinedex series, TK-16, H-Pinedex (H-PDX)(all of the above products are trademarks and available from Matsutani Chemical Industry Co., Ltd.)

Bone filling material of the present invention is prepared by mixing sintered titanium dioxide and dextrin in an appropriate ratio and further mixing with purified water or physiological saline to make a composition in the form of a paste or dumpling for final use.

An amount of each component is not limited to specific one as long as a material in the form of a paste or dumpling is prepared. However, the bone filling material comprises preferably 0.5 to 10 parts by weight, more preferably 0.8 to 5 parts by weight of the dextrin and preferably 70 to 170 parts by weight, more preferably 80 to 150 parts by weight of water per 100 parts by weight of the sintered titanium dioxide.

It may be possible to add sintered titanium dioxide to dextrin solution previously prepared or to mix all components in given amounts at once.

When sintered titanium dioxide is added to dextrin solution previously prepared, a concentration of the dextrin solution is not limited to specific one but it is preferably about 1% to about 3% (W/V) in light of osmotic pressure and safety.

An amount of the sintered titanium dioxide added to the about 1 to about 3% (W/V) dextrin solution is preferably about 600 mg to about 1200 mg. If the amount is lower, the product may show flowability, while if it is higher, it may be difficult to make a bulk.

It is also possible to mix water, dextrin and sintered titanium dioxide at once just before the final use. It is possible to make sintered titanium dioxide-dextrin complex previously. It is also possible for a doctor on clinical site to adjust a mixing ratio, an amount of the complex, a viscosity (or hardness) of the complex so that they are adapted to the volume and the site of bone defects and the like, when the doctor fills the bone defects with the bone filling material.

Water used in the present invention is preferably purified water and physiological saline. A mixture may be sterilized after all the components are mixed, or each of all the components may be previously sterilized and mixed just before the use.

The bone filling material of the present invention may be a mixture of sintered titanium dioxide, dextrin and water only but may contain other bone filling materials, for example, calcium phosphate powder or granule such as tri-calcium phosphate powder or granule and hydroxyapatite. An amount of other bone filling materials to be added is arbitrarily determined taking into consideration effects and overall handling property and the like. Generally, the amount is 100 parts by weight or less per 100 parts by weight of a mixture of sintered titanium dioxide, dextrin and water only.

It may be possible to add growth factors such as BMP, FGA, TGFβ, PDGF, and VEGF, hormones such as PTH, and prostaglandin and peptide formulations. An amount of the additives to be added is arbitrarily determined taking into consideration effects and the like. Generally, the amount is 50 parts by weight or less per 100 parts by weight of a mixture of sintered titanium dioxide, dextrin and water only.

The effects of the present invention will be explained with reference to the following examples to which the scope of the present invention is not limited.

Example 1

Effects of Dextrin on Mouse Osteoblast-Like Cells (Biocompatibility Test) If dextrin is administered or implanted in the body as an implant material, it is essential for the dextrin to have good biocompatibility with the body tissues. Assuming that dextrin is implanted in the body, effects of dextrin on mouse osteoblast-like cells were examined in vitro.

(1) Materials:

Dextrin having weight average molecular weight of 2,000 (Matsutani Chemical Industry Co., Ltd, Pinefiber (trademark)) was used in this experiment.

(2) Cell proliferation Test

MC3T3-E1 derived from mouse osteoblast-like cells has been widely used in researches as a cell which proliferates, differentiates and calcifies to reflect bone formation process in the body similar to bone cells in the body.

For this reason, also in this experiment, MC3T3-E1 (Dainippon Sumitomo Pharma Co., Ltd.) derived from mouse osteoblast-like cells was used for cell proliferation test.

A medium was prepared by adding 10 wt % bovine fetal serum (EQUITECH-BIO), and 100 U/ml Penicillin-100 μg/ml Streptomycin(GIBCO) to α-Minimum Essential Medium (GIBCO).

The experimental group consisted of those in which 0.1, 1.0, and 10 mmol/l of dextrin had each been added to the medium, while the control group used only the medium.

The cell culture was adjusted so that MC3T3-El would be $1 \times 10^4$ cells/ml, 400 μl each of which was seeded onto a 24-well microplate. Each group was then cultured under conditions of 37° C. and 5% $CO_2$ concentration over a culture periods varying from 1, 3, 5, and 7 days. Each of the medium was replaced every two day.

The Cell Counting Kit-8 (Dojindo) was used to measure the number of living cells. Namely, the culture liquid in each well cultured for 1, 3, 5 or 7 days was replaced by a fresh culture liquid and 40 μl of the Cell Counting Kit-8 agent was added to the each well. After left to stand for one hour, each 100 μl was placed in 96-well plate and absorbance at 450 nm was measured by a microplate reader. The number of living cells was obtained from a calibration curve which was prepared by providing a given number of cells ($1 \times 10^4$ to $70 \times 10^4$ cells/ml) and measuring absorbance (n=5).

(3) Alkaline Phosphatase Activity

Alkaline phosphatase is one of glycosylphosphatidylinositol (GPI) anchor proteins in the cell membrane surface and is known as an index of bone formation process.

For the reasons, also in this experiment, alkaline phosphatase (ALP) was measured to evaluate differentiation potency of MC3T3-E1 during bone formation.

The alkaline phosphatase activity (hereinafter, ALP activity) was evaluated using Lab Assay™ ALP (Wako Pure Chemical Industries, Ltd.) which was based on the Bessey-Lowry method.

The method for culturing was the same as mentioned above and the period of culturing was 5, 7, 9, and 11 days.

After the culturing was completed, 20 μl of each culture liquid was placed in 96-well microplate, to which 0.1 mol/l carbonate buffer (pH9.8) containing 2.0 mmol/l of magnesium chloride and 6.7 mmol/l of p-nitrophenyl phosphoric acid was mixed and reacted at 37° C. for 15 minutes. Then, 0.2 mol/l sodium hydroxide solution was added to stop the reaction. Absorbance at 405 nm was measured by a microplate reader and ALP activity was obtained from a calibration curve to convert into an amount of p-nitrophenol formed (n=3).

(4) Statistical Analysis

Multiple comparison test by Tukey method was used for statistical analysis of the number of living cells and ALP activity at each culturing period.

(5) Results

Cell proliferation test using MC3T3-E1

Figure 1:
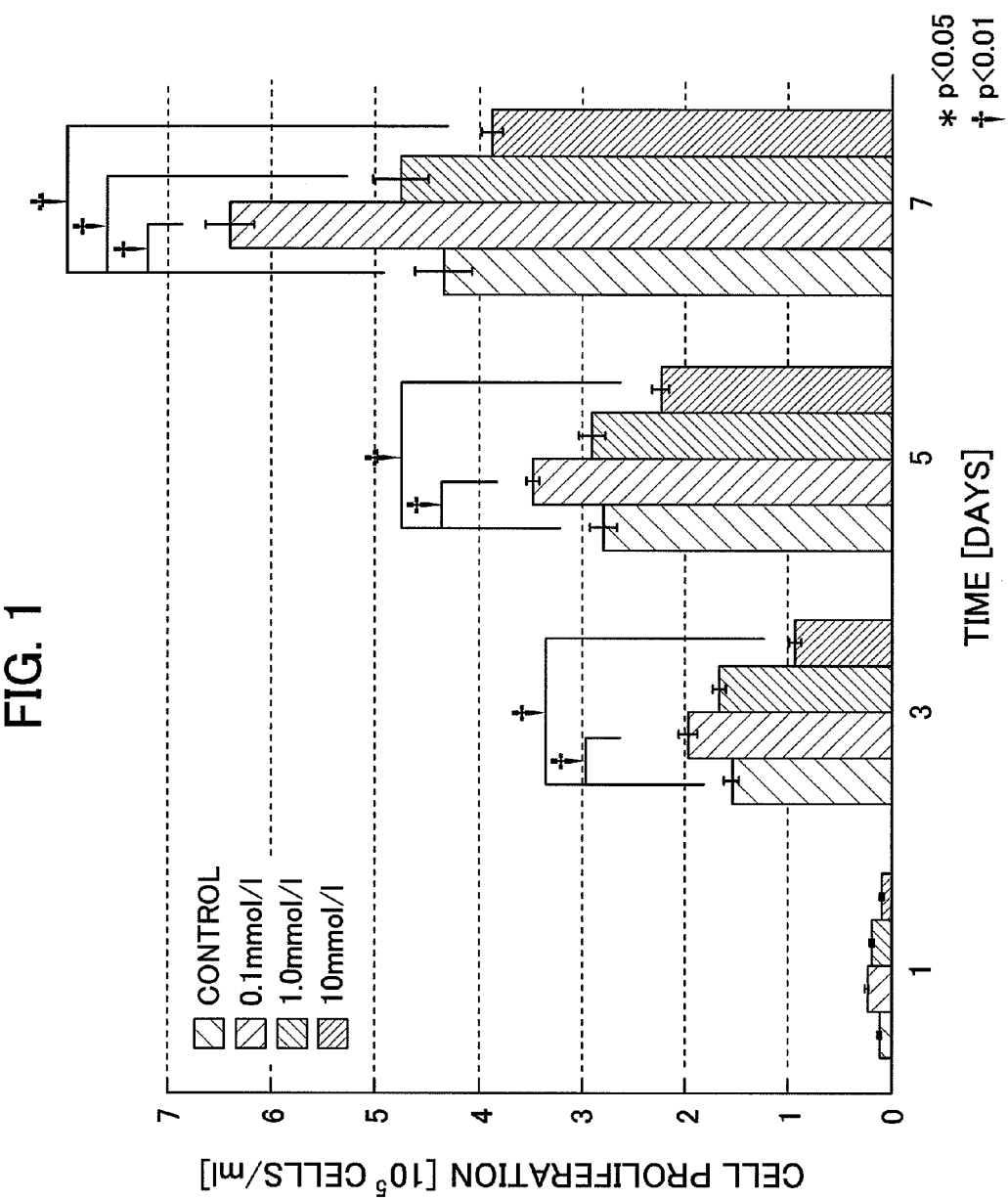
FIG. 1 shows the results of proliferation test of mouse osteoblast-like cells cultured in a medium to which dextrin was added.

The results of cell proliferation test wherein dextrin was added to the culture liquid is shown in FIG. 1. Cell proliferation was observed for all Experimental groups and Control with time of culture period.

The 0.1 mmol/l addition group showed higher value than Control after 3 days.

Statistical significance was confirmed.

The 1.0 mmol/l addition group showed higher value than Control after 7 days.

Statistical significance was confirmed.

The 10 mmol/l addition group showed significantly lower value than Control after 3 days.

(6) ALP Activity

Figure 2:
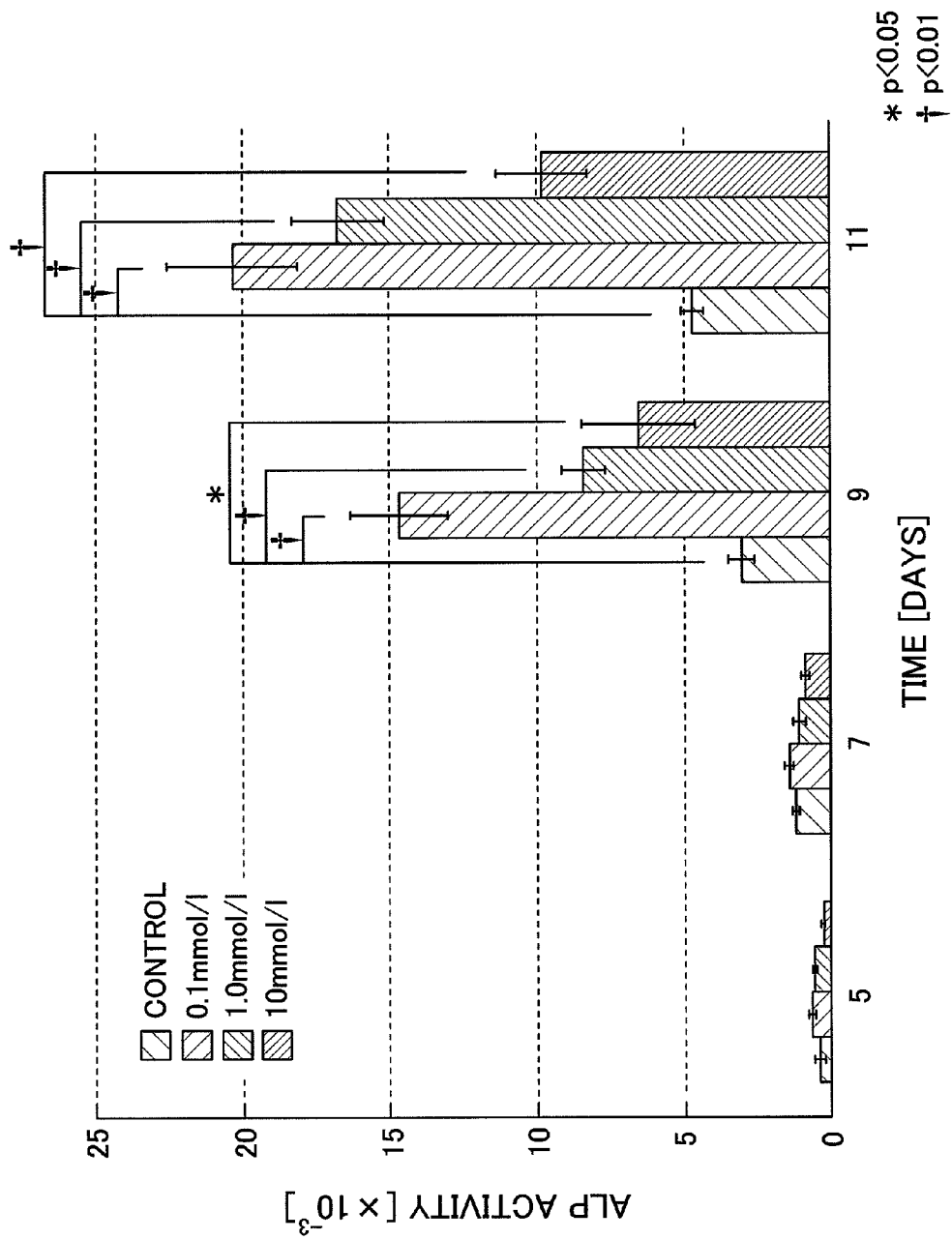
FIG. 2 shows the results of alkaline phosphatase activity test of mouse osteoblast-like cells.

The results of ALP activity in MC3T3-E1 are shown in FIG. 2. The ALP activity was slightly observed for all the groups after the culture of 5 and 7 days but there was no significant difference. After 9 days and 11 days, all of the 0.1, 1.0, and 10 mmol/l addition groups showed remarkably and significantly higher ALP activity than Control.

Example 2

Bone filling evaluation of sintered titanium dioxide-dextrin complex (1) Preparation of Sintered Titanium Dioxide As titanium dioxide, titanium dioxide powder (Ishihara Sangyo Kaisha Ltd. FTL-100) having average particle width of 0.3 μm and average particle length of 5.0 μm was used. The sample was heated in an electric furnace (Koyo Thermo System Co., Ltd., LP-907) from room temperature to 100° C. in 30 minutes to dry the sample, which was then heated to a given sintering temperature in 120 minutes to sinter the sample. Sintering was conducted under atmospheric condition at 1400° C. After the sample was kept in the furnace at the given temperature for 30 minutes, it was cooled in the furnace and used for the experiments. The sample was sterilized in an autoclave at 120° C. for 15 minutes.

(2) Observation of the Surface Texture of Sintered Titanium Dioxide Sintered titanium dioxide was observed for particle size, the surface texture and morphology under a scanning electron microscope (SEM; JSM-5900LV, JEOL Ltd.) at acceleration voltage of 10 kV.-

(3) Preparation of Sintered Titanium Dioxide-Dextrin Complex

Handling property of a mixture obtained by suspending sintered titanium dioxide in 2% (W/V) indigestible dextrin aqueous solution To one ml of 2% (W/V) indigestible dextrin solution (in physiological saline), sintered titanium dioxide prepared in the above step (1) was added in various amounts and resulting mixtures (complexes) were evaluated for flowability, and handling properties (easiness of filling in defects and flowability). The results are shown in the following table.

| Added amount of sintered titanium dioxide | Flowability and handling properties of complexes |
|---|---|
| 200 mg | High flowability and bad handling properties |
| 400 mg | High flowability and bad handling properties |
| 600 mg | Adequate flowability and good handling properties |
| 800 mg | Adequate flowability and good handling properties |
| 1200 mg | Fair flowability and fair filling property |
| 1600 mg | No bulk formation and bad filling property |
| 4000 mg | No bulk formation and bad filling property |

Taking the above test results into consideration, sintered titanium dioxide-dextrin complex was prepared as follows.

Dextrin (weight average molecular weight=2000) was dissolved in physiological saline (Otsuka Pharmaceutical Co., Ltd.) to prepare 10 mmol/l (2% W/V) dextrin solution. To 0.05 ml of the dextrin solution, 40 mg of sintered titanium dioxide was added and mixed to prepare sintered titanium dioxide-dextrin complex.

BONE JECT® (Koken Co., Ltd.) which has been clinically applied in dental field was used as Control. BONE JECT® is a mixed material of sintered bone and atelocollagen solution (2% bovine skin derived atelocollagen solution in phosphate buffer) in a weight ratio of 3:2, wherein the sintered bone is prepared by removing soft tissue from frozen bovine bone, boiling and chemical deproteinizing followed by sintering in an electric furnace at a high temperature of 1100 to 1450° C. and keeps the form of mainly cancellous bone as it is.

(4) Experiments of Implant to Bone Defects of Rabbit' Femur

Six-week-old Japanese white rabbits (male: body weight of about 1.0 kg to 1.4 kg) were anesthetized by Somnopentyl® (Kyoritsu Seiyaku Corporation) intravenous sedation method to make general anesthesia state under which indolent treatment was conducted. The operated area was sterilized, shaved and locally anesthetized by lidocaine hydrochloride (2% Xylocaine epinephrine).

Skin in left femur was incised and skin and fascia were peeled off without damaging muscle tissue to expose void in the femur fascia.

The bone defects (diameter 2.0 mm, depth about 1.0 mm) were made on lateral epicondyles of the femur by carbite bar or round bar up to bone marrow.

Then, 5 mg of sintered titanium dioxide-dextrin complex prepared in the above step (3) was filled into the bone defects using a 1.0 ml syringe (TERUMO) and the incised area was sutured.

Similarly, the same amount of BONE JECT® was filled into the bone defects.

The rabbits were bred for one or six weeks after filling.

After breeding for the given periods, the rabbits were sacrificed by intravenously injecting Somnopentyl®. The femur was excised and fixed in 10% neutral buffered formalin solution for two weeks. Non-decalcified samples were prepared from the fixed femur samples. First, they were dehydrated by ethanol ascending series and resin-embedded by a mixture of methyl methacrylate monomer (Wako Pure Chemical) and dimethyl 2,2'-azobis(isobutyrate) (Wako Pure Chemical). The resin block was sliced by low revolution diamond cutter using Saw microtome for hard tissue (LEICA SP1600) to obtain the femur and filling area of about 50 µm in thickness.

Further, the samples were stained by hematoxylin and eosin (H-E stain) for histological evaluation under optical microscope.

This experiment has been approved by Research Ethics Committee for Animal Experiments in Aichi Gakuin University (AGUD037).

(5) Analysis by Electron Probe Micro Analyzer

The samples six weeks after filling were observed under Electron Probe Micro Analyzer (EPMA; JXA-8530FA, JEOL Ltd.) at acceleration voltage of 10 kV.

(6) Results (i) Observation of the Surface Texture of Sintered Titanium Dioxide

Figure 3:
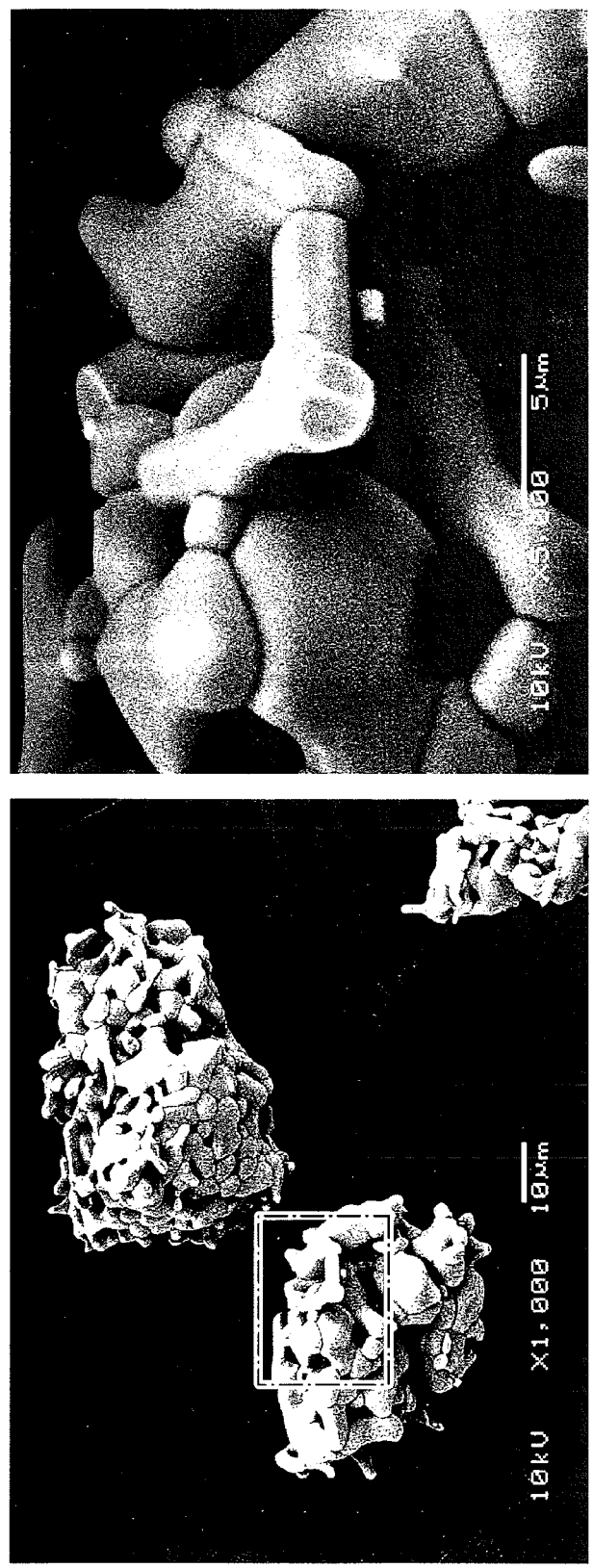
FIG. 3 shows the surface texture of sintered titanium dioxide observed under a scanning electron microscope (SEM). The right figure is a macrograph of the framed area of the left figure.
Figure 4A:
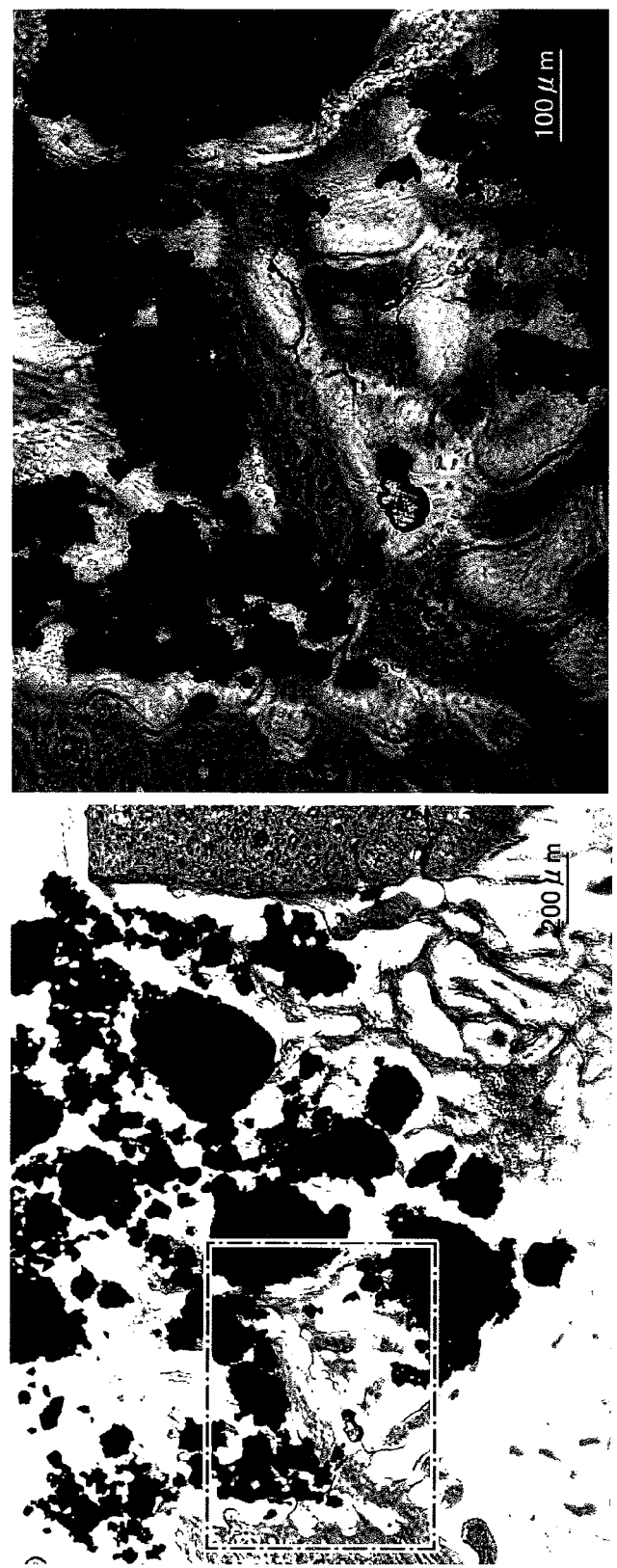
Figure 4B:
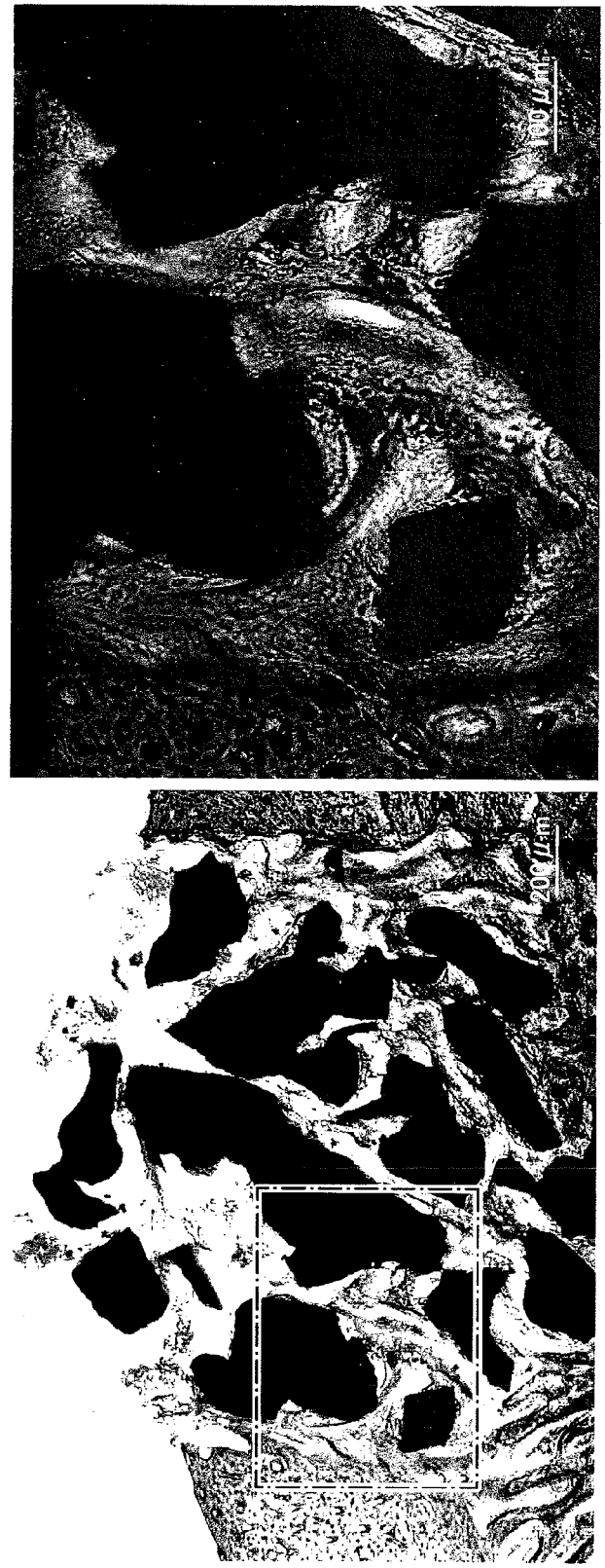
Figure 4C:
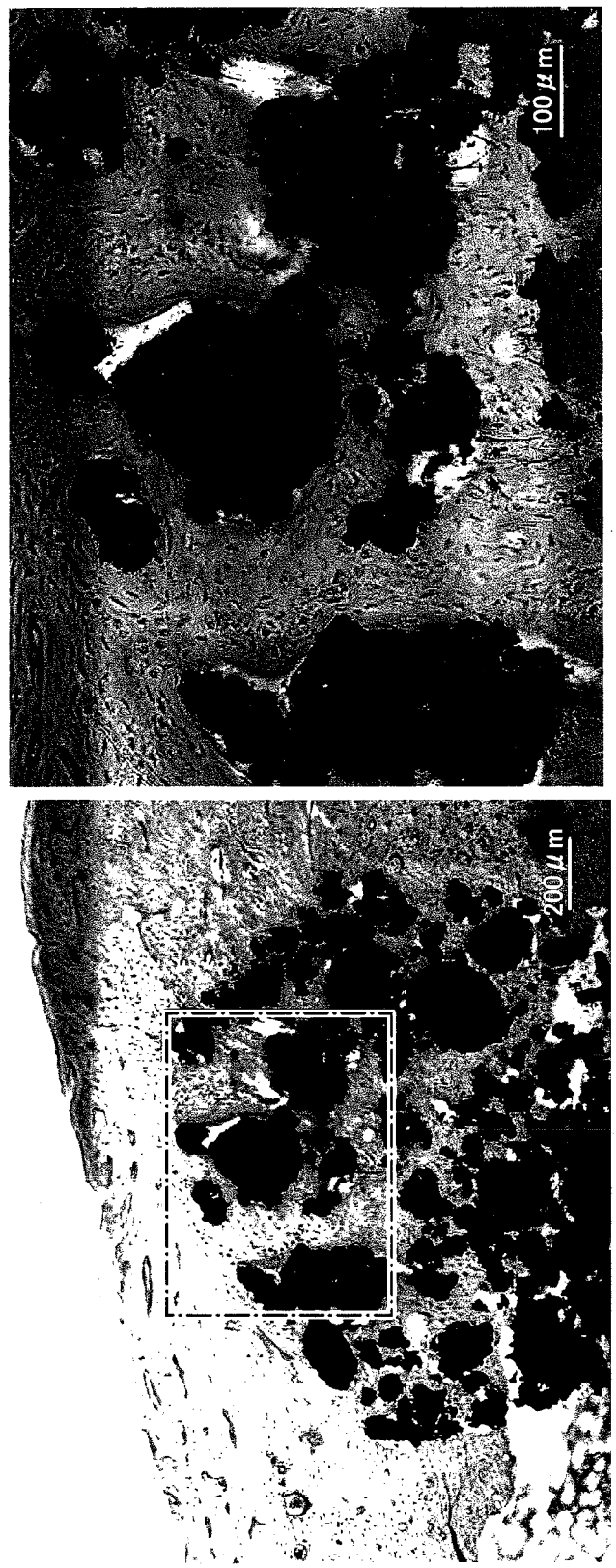
Figure 4D:
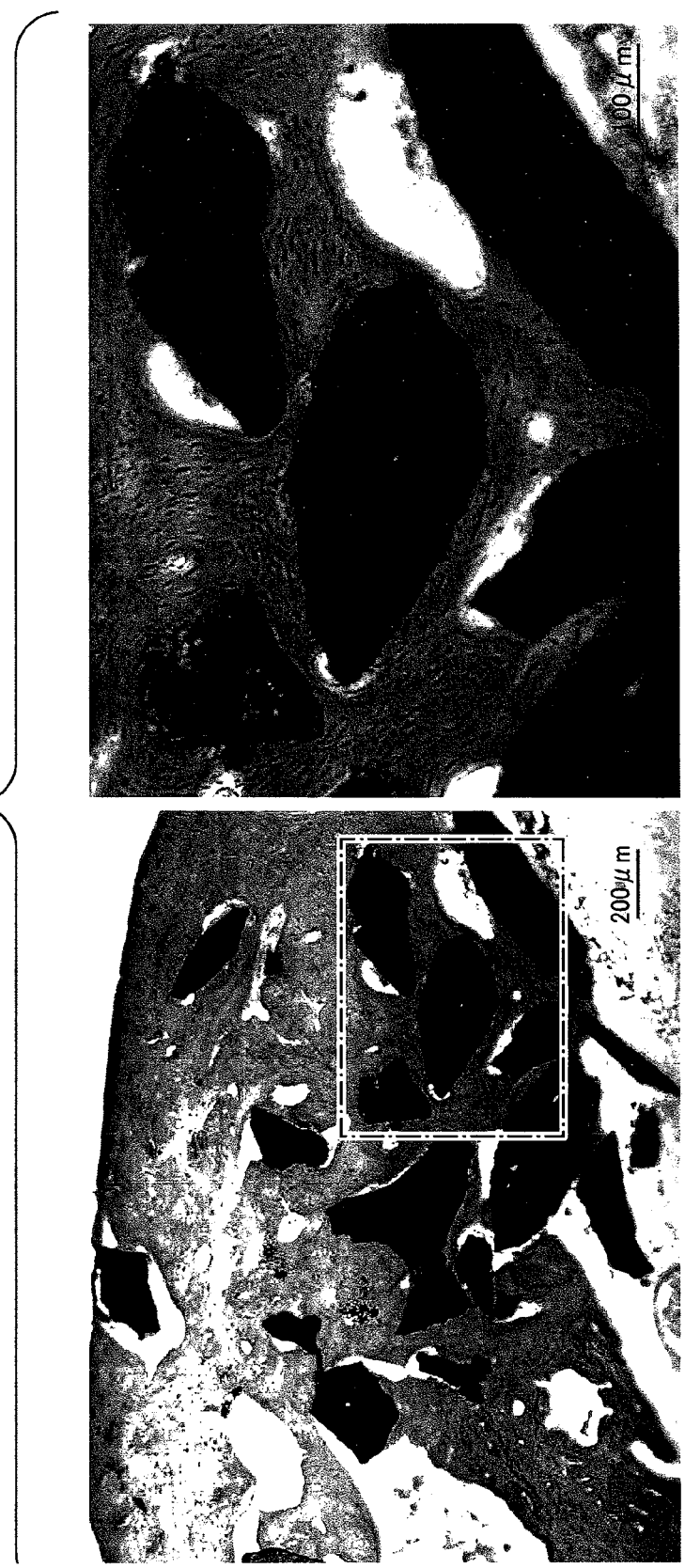

SEM observation revealed that sintered titanium dioxide particles have a diameter of about 10 to 50 µm, bind with each other and are porous (FIG. 3).

(ii) Histological Observation of Bone Filling Area

Histological observation of bone tissues one week after implantation revealed that the bone tissue was firmly filled with sintered titanium dioxide-dextrin complex (FIG. 4A) or BONE JECT® (FIG. 4B) but was almost not reconstructed. Meanwhile, six weeks after implantation, it was observed that bone tissues were clearly reconstructed between particles for both the samples (FIG. 4C (sintered titanium dioxide-dextrin complex) and FIG. 4D (BONE JECT®)).

In FIGS. 4A to 4D, black area shows bone filling material surrounded by gray bone tissue. Six weeks after implantation, it was clearly observed that bone tissues were reconstructed around the bone filling materials.

(iii) EPMA Analysis

Six weeks after implantation, color mapping and composite mapping of the samples showed that Ca and P were present in porous inner areas between the sintered titanium dioxide particles (FIGS. 5A and 5B).

The results show that the sintered titanium dioxide-dextrin complex imparts sufficient shape in lacunae or bone defects and has excellent bone conduction capability. Namely, the sintered titanium dioxide-dextrin complex stimulates proliferation of osteogenic cells and synthesis of collagen fiber to promote bone formation.

In FIGS. 5A and 5B, black areas show the presence of Ca, P and Ti.

The lower right figure in FIG. 5A shows graphic overlay of Ca, P and Ti and the lower right figure in FIG. 5B shows graphic overlay of Ca and P.

In the BONE JECT® sample, Ca and P are recognized but do not move into granules.

In contrast, the sintered titanium dioxide-dextrin complex is porous and graphic overlay of enlarged photos shows the presence of Ca and P inside Ti. This confirms that the sintered titanium dioxide-dextrin complex has bone conduction capability.

The above results confirm that dextrin has excellent cell compatibility and biocompatibility and shows good shape-imparting property when it is combined with sintered titanium dioxide to form a complex.

What is claimed is:

1. A bone filling material comprising sintered titanium dioxide, water and dextrin, wherein titanium dioxide is the only metal oxide in the bone filling material and the bone filling material comprises 0.5 to 10 parts by weight of the dextrin and 70 to 170 parts by weight of water, each per 100 parts by weight of the sintered titanium dioxide.

2. The bone filling material of claim 1, wherein the sintered titanium dioxide is of rutile-type.

3. The bone filling material of claim 1, wherein the dextrin is indigestible dextrin or its hydrogenated product, said indigestible dextrin having α-1,6-glycosidic bonds, α-1,2-glycosidic bonds and α-1,3-glycosidic bonds in addition to α-1,4-glycosidic bonds in its structure.

4. A method for reconstructing bone defects which comprises filling the bone defects in an animal with a bone filling material comprising sintered titanium dioxide, water and dextrin, wherein titanium dioxide is the only metal oxide in the bone filling material and the bone filling material comprises 0.5 to 10 parts by weight of the dextrin and 70 to 170 parts by weight of water, each per 100 parts by weight of the sintered titanium dioxide.

5. The method of claim 4, wherein the sintered titanium dioxide is of rutile-type.

6. The method of claim 4, wherein the dextrin is indigestible dextrin or its hydrogenated product, said indigestible dextrin having α-1,6-glycosidic bonds, α-1,2-glycosidic bonds and α-1,3-glycosidic bonds in addition to α-1,4-glycosidic bonds in its structure.

7. The bone filling material of claim 1, wherein the bone filling material comprises 1.7 to 3 parts by weight of the dextrin per 100 parts by weight of the sintered titanium dioxide.

8. The method of claim 4, wherein the bone filling material comprises 1.7 to 3 parts by weight of the dextrin per 100 parts by weight of the sintered titanium dioxide.

* * * * *